US012631498B2

(12) United States Patent
Wyatt

(10) Patent No.: US 12,631,498 B2
(45) Date of Patent: May 19, 2026

(54) SELF-CALIBRATION OF A POLYMER-BASED HUMIDITY SENSOR

(71) Applicant: TEXAS INSTRUMENTS INCORPORATED, Dallas, TX (US)

(72) Inventor: Joshua Daniel Wyatt, McKinney, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 495 days.

(21) Appl. No.: 17/747,272

(22) Filed: May 18, 2022

(65) Prior Publication Data

US 2022/0373402 A1     Nov. 24, 2022

Related U.S. Application Data

(60) Provisional application No. 63/190,273, filed on May 19, 2021.

(51) Int. Cl.
| | |
|---|---|
| *G01K 3/00* | (2006.01) |
| *G01K 15/00* | (2006.01) |
| *G01N 27/12* | (2006.01) |
| *G01N 33/00* | (2006.01) |

(52) U.S. Cl.
CPC .......... *G01K 3/005* (2013.01); *G01K 15/005* (2013.01); *G01N 27/121* (2013.01); *G01N 33/0006* (2013.01)

(58) Field of Classification Search
CPC ............. G01N 33/0006; G01N 27/121; G01N 27/225; G01N 33/0031; G01N 33/007; G01N 25/18; G01K 3/005; G01K 15/005; H05B 3/0019; F24F 2110/20; G01D 18/008; G01D 23/20
See application file for complete search history.

(56) References Cited

U.S. PATENT DOCUMENTS

| | | | |
|---|---|---|---|
| 2018/0143084 A1* | 5/2018 | Diether | G01D 3/022 |
| 2019/0145834 A1* | 5/2019 | Nakamura | G01K 7/16 |
| | | | 374/164 |
| 2019/0195820 A1* | 6/2019 | Fornasari | G01N 27/223 |
| 2020/0049644 A1* | 2/2020 | Wu | G01N 27/123 |
| 2022/0178862 A1* | 6/2022 | Leppänen et al. | G01N 27/225 |

FOREIGN PATENT DOCUMENTS

JP          2014085154 A   *   5/2014

* cited by examiner

*Primary Examiner* — Catherine T. Rastovski
*Assistant Examiner* — Carter W Ferrell
(74) *Attorney, Agent, or Firm* — Xianghui Huang; Frank D. Cimino

(57)          ABSTRACT

Self-calibrating a humidity sensor of an integrated humidity and temperature sensor, using the integrated heating element, and the temperature and humidity sensors, of the device, together with a firmware-based control loop running on a controller. The controller actively calculates and monitors one or both sensor output, and the slopes of the sensor outputs, in real time, while the heating element is on, and compares one or both slopes to a pre-programmed threshold, while in a programmable control loop, to then capture the appropriate relative humidity offset to apply to the device during normal operation (with the integrated heating element switched off) for correcting the relative humidity output from the device. Any singularly mounted in-system device can be calibrated, independent of external references, for in-system calibration.

16 Claims, 6 Drawing Sheets

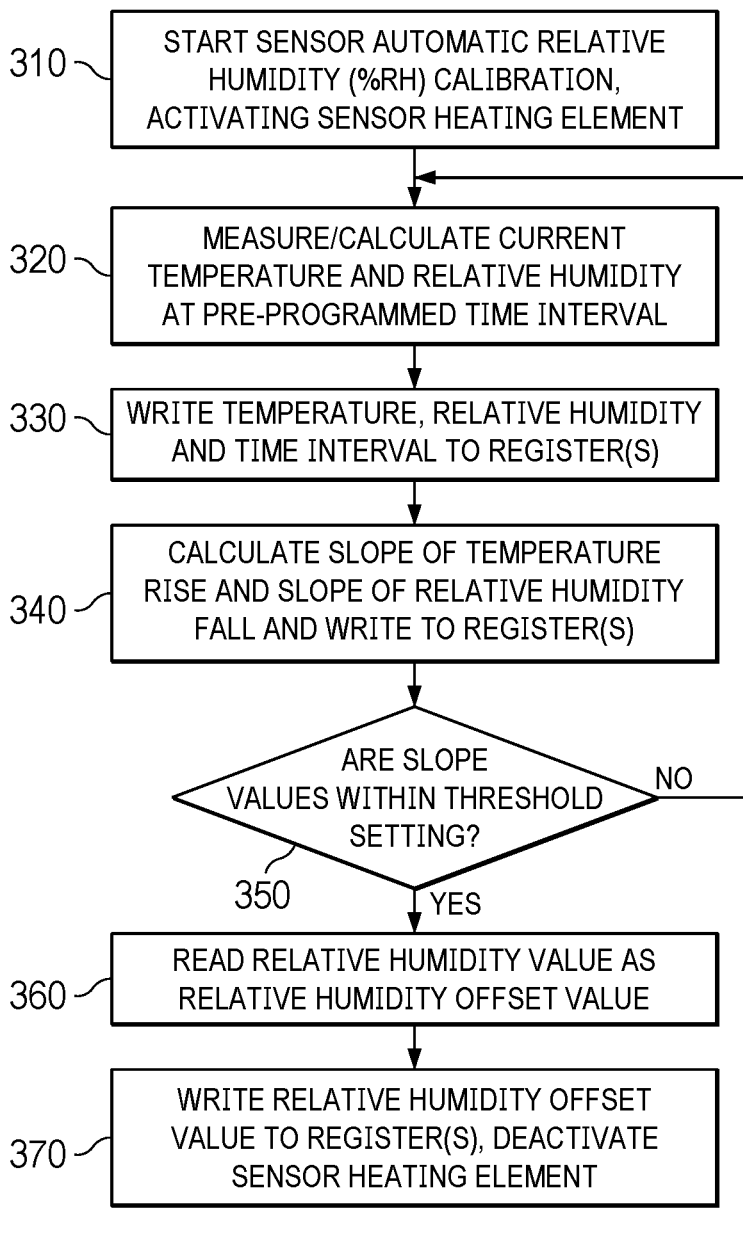

310 START SENSOR AUTOMATIC RELATIVE HUMIDITY (%RH) CALIBRATION, ACTIVATING SENSOR HEATING ELEMENT

320 MEASURE/CALCULATE CURRENT TEMPERATURE AND RELATIVE HUMIDITY AT PRE-PROGRAMMED TIME INTERVAL

330 WRITE TEMPERATURE, RELATIVE HUMIDITY AND TIME INTERVAL TO REGISTER(S)

340 CALCULATE SLOPE OF TEMPERATURE RISE AND SLOPE OF RELATIVE HUMIDITY FALL AND WRITE TO REGISTER(S)

350 ARE SLOPE VALUES WITHIN THRESHOLD SETTING? NO

YES

360 READ RELATIVE HUMIDITY VALUE AS RELATIVE HUMIDITY OFFSET VALUE

370 WRITE RELATIVE HUMIDITY OFFSET VALUE TO REGISTER(S), DEACTIVATE SENSOR HEATING ELEMENT

FIG. 3

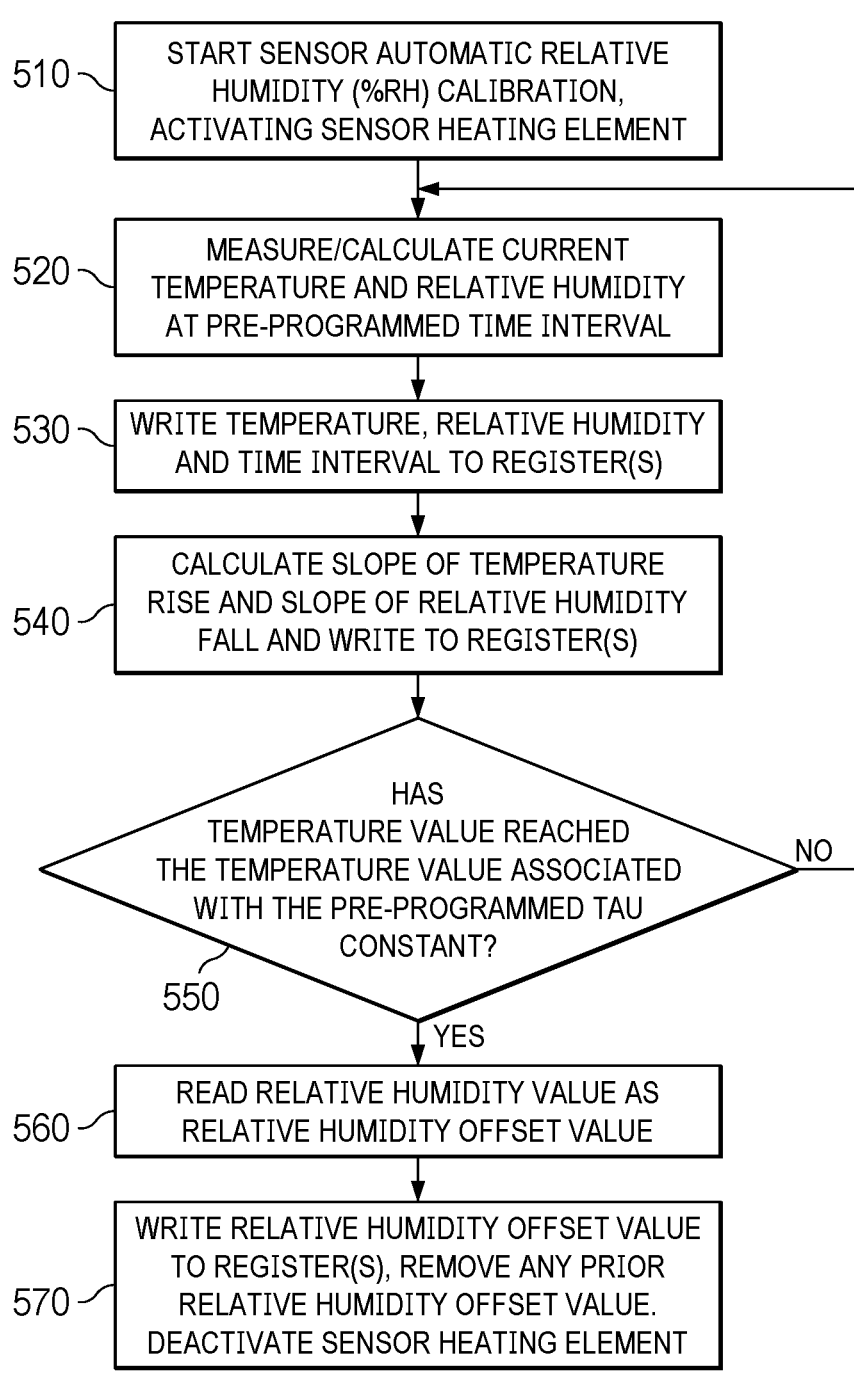

510 — START SENSOR AUTOMATIC RELATIVE HUMIDITY (%RH) CALIBRATION, ACTIVATING SENSOR HEATING ELEMENT

520 — MEASURE/CALCULATE CURRENT TEMPERATURE AND RELATIVE HUMIDITY AT PRE-PROGRAMMED TIME INTERVAL

530 — WRITE TEMPERATURE, RELATIVE HUMIDITY AND TIME INTERVAL TO REGISTER(S)

540 — CALCULATE SLOPE OF TEMPERATURE RISE AND SLOPE OF RELATIVE HUMIDITY FALL AND WRITE TO REGISTER(S)

550 — HAS TEMPERATURE VALUE REACHED THE TEMPERATURE VALUE ASSOCIATED WITH THE PRE-PROGRAMMED TAU CONSTANT?

NO

YES

560 — READ RELATIVE HUMIDITY VALUE AS RELATIVE HUMIDITY OFFSET VALUE

570 — WRITE RELATIVE HUMIDITY OFFSET VALUE TO REGISTER(S), REMOVE ANY PRIOR RELATIVE HUMIDITY OFFSET VALUE. DEACTIVATE SENSOR HEATING ELEMENT

| VOLTAGE 610 | PEAK CURRENT (mA) 620 | STABLE CURRENT (Ma) 630 | FINAL TEMP 640 | FINAL %RH 650 | FINAL %RH VALUE DIVISOR 660 | RESULTING OFFSET VALUE TO APPLY 670 | VARIANCE FROM KNOWN GOOD VALUE 680 |
|---|---|---|---|---|---|---|---|
| 3.3 | 99 | 92 | 73.48 | 9.82 | 1 | 9.82 | 0 |
| 3 | 90 | 86 | 66.33 | 11.82 | 1.25 | 9.456 | 0.257386868 |
| 2.7 | 82 | 78 | 58.79 | 14.88 | 1.5 | 9.92 | 0.070710678 |
| 2.4 | 74 | 70 | 51.73 | 19.42 | 2 | 9.71 | 0.077781746 |
| 2.1 | 63 | 61 | 45.5 | 24.18 | 2.5 | 9.672 | 0.104651804 |
| 1.8 | 54 | 52 | 39.47 | 30.59 | 3 | 10.19666667 | 0.266343554 |

SELF-CALIBRATION OF A POLYMER-BASED HUMIDITY SENSOR

RELATED APPLICATION

This application claims priority to U.S. Provisional Application Ser. No. 63/190,273, filed May 19, 2021, which application is incorporated herein by reference.

BACKGROUND

Relative humidity (RH) sensors, similar to other sensors, even if ideally calibrated in production, can deviate from ideal behavior over time and/or if exposed to conditions outside a normal operative range (e.g., high temperature, high humidity, or contaminant conditions). Sensor response is affected by cross-sensitivities, such as environmental conditions (typically temperature, but, depending on the sensor, other parameters such as pressure or gas concentration). In addition to typical non-ideal conditions, some sensors suffer from aging (e.g., an offset in accuracy due to time in use and/or to exposure to contaminants). In short, sensors accumulate offset with aging and this offset detrimentally impacts the accuracy of their measurements.

SUMMARY

In one aspect, a method using the integrated heater feature of a humidity and temperature sensor hardware construction to derive a humidity offset needed by each singularly mounted in-system device, independent of external references, for in-system calibration. Active calculation of slope of one or both sensor outputs (humidity and temperature) is performed and the respective output is compared to a pre-programmed threshold while in a programmable control loop.

In another aspect, the disclosed embodiments provide a method to efficiently implement a self-contained system calibration to any end product using the respective humidity sensors. The described solutions are applied at any time, at room temperature, without needing external test equipment or an environmental chamber. Firmware associated with the device offers two variables which are programmable (slope of temperature rise and slope of relative humidity (% RH) fall), for precision tuning of the self-calibration solution during sensor development/characterization, to exactly match end product sensor design to a precision reference.

In accordance with one example, a method of calibrating a humidity sensor formed adjacent to a heating element and a temperature sensor over a semiconductor substrate includes turning on a heating element, upon initiation of humidity sensor calibration, thereby increasing temperature of the humidity sensor; measuring a device temperature, by the temperature sensor, indicative of a temperature of the humidity sensor at certain points in time; measuring a humidity value indicative of a relative humidity at the humidity sensor at the certain points in time; calculating a slope of the device temperature at the certain points in time; and determining a relative humidity offset value responsive to the slope of the device temperature becoming less than a threshold value.

In other examples, the relative humidity offset value represents humidity sensor calibration, and the method further comprises subtracting the relative humidity offset value from the humidity value measured at any point in time, during normal humidity sensing operations, to provide a relative humidity value. In another example, the method also includes storing the relative humidity offset value to a register associated with the humidity sensor and the temperature sensor for use in determining relative humidity values. In an alternative example, the method also includes storing the relative humidity offset value to a memory of a controller associated with the humidity sensor and the temperature sensor for use in determining relative humidity values. In another example, the method further comprises determining that the slope of temperature rise is less than a threshold value. In still another example, the threshold value of the slope of temperature value rise is satisfied when the slope of the temperature value rise equals, or is very close to, zero.

In accordance with another example, the method of calibrating the humidity sensor includes calculating a slope of the humidity value at the certain points in time, monitoring the slope of humidity value, over the certain points in time; and wherein, upon the slope of the humidity value reaching a threshold value, recording the humidity value at that respective point in time as the relative humidity offset value.

In one aspect of the preceding example, the method of calibrating a humidity sensor also includes subtracting the relative humidity offset value from the humidity value measured at any point in time, during normal humidity sensing operations, to provide a relative humidity value. In another aspect of this example, the threshold value of the slope of the humidity value fall, and the threshold value of the slope of the temperature value rise, are each satisfied when the respective slope equals, or is very close to, zero.

In accordance with a further example, a controller is configured to cause a heater to change a temperature of a humidity sensor and to calibrate the humidity sensor, the controller comprising a central processing unit operable to be coupled to the heater and the humidity sensor; and memory coupled to the central processing unit; and wherein the controller is operable to determine a relative humidity offset value of the humidity sensor responsive to the change of the temperature of the humidity sensory becoming less than a threshold value. In another example, the controller is configured to store the relative humidity offset value in a memory therein, and to subtract the relative humidity offset value from the humidity value measured at any point in time, during normal humidity sensing operations, to provide a relative humidity value.

In one aspect of the preceding example, to determine the relative humidity offset value of the humidity sensor, the controller is configured to turn on a heating element associated with the humidity sensor, upon initiation of humidity sensor calibration, thereby increasing temperature of the humidity sensor; measure a temperature value indicative of a temperature of the humidity sensor at certain points in time; measure a humidity value indicative of a relative humidity at the humidity sensor at each of the certain points in time; calculate a slope of temperature value rise at the certain points in time; monitor the slope of temperature value, and, upon reaching the threshold value of the slope of temperature value, record the humidity value at that respective point in time as a relative humidity offset value. Further, the threshold value of the slope of temperature value rise is satisfied when the slope of the temperature value rise equals, or is very close to, zero.

In another aspect of the preceding example, to determine the relative humidity offset value of the humidity sensor, the controller is configured to calculate a slope of humidity value at the certain points in time; monitor the slope of humidity value; upon reaching the threshold value of the slope of humidity value, record the humidity value at that respective point in time as the relative humidity offset value; and to subtract the relative humidity offset value from the humidity value measured at any point in time, during normal humidity sensing operations, to provide a relative humidity value.

In other examples, the slope of temperature value equals approximately zero when at a final, maximum temperature of the humidity sensor, and the threshold value of the slope of temperature value is selected from the group consisting of 0.01%, 0.1%, 0.5%, and 1%, of final, maximum temperature.

In accordance with a still further example, a system includes a humidity sensor formed over a semiconductor substrate and configured to output a signal corresponding to a humidity value; a temperature sensor formed over the semiconductor substrate and adjacent to the humidity sensor, the temperature sensor configured to determine a temperature of the humidity sensor, a heating element formed over the semiconductor substrate and adjacent to the humidity sensor and the temperature sensor, the heating element configured to change the temperature of the humidity sensor; and a controller coupled to the humidity sensor, the temperature sensor, and the heating element. The controller is configured to change the temperature of the humidity sensor; calculate a rate of change of temperature of the humidity sensor; calculate a relative humidity offset value responsive to the rate of change of temperature of the humidity sensor reaching a threshold value, and calculate a relative humidity value responsive to a measured humidity value by the humidity sensor and the calculated relative humidity offset value.

In one aspect of the preceding example, the controller is further configured to calculate a slope of humidity value at the certain points in time; monitor the slope of humidity value; upon reaching the threshold value of the slope of humidity value and the threshold value of the slope of temperature value rise, record the humidity value at that respective point in time as the relative humidity offset value; wherein, to calculate the relative humidity value, the controller is further configured to subtract the relative humidity offset value from the measured humidity value, at any point in time, during normal humidity sensing operations, to provide the relative humidity value.

BRIEF DESCRIPTION OF THE DRAWINGS

For a detailed description of various examples, reference will now be made to the accompanying drawings in which:

FIG. 3 is a flow chart illustrating a method of humidity sensor calibration, in accordance with various examples;

FIG. 5 is a flow chart illustrating another method of humidity sensor calibration, in accordance with various examples; and FIG. 6 illustrates an association table attributable to an example humidity and temperature sensor, where various operational input voltage values of the sensor are associated with final temperature and % RH obtained at the respective input voltages, to obtain a proper humidity offset value.

The same reference numbers or other reference designators are used in the drawings to designate the same or similar (functionally and/or structurally) features.

DETAILED DESCRIPTION

Figure 1:
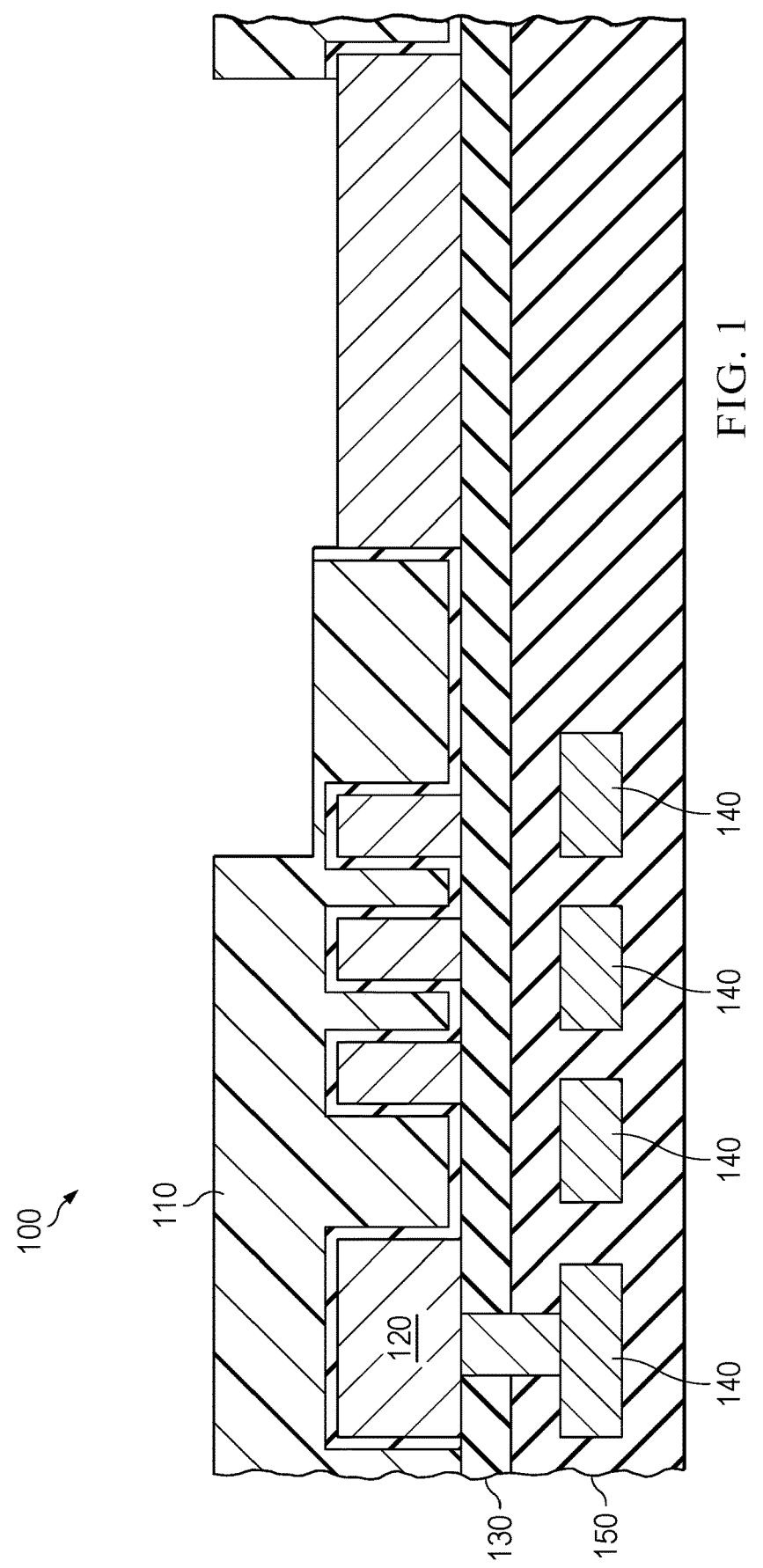
FIG. 1 is a cross-sectional diagram of an integrated humidity and temperature sensor, in accordance with various examples.

Specific aspects and examples will now be described in detail with reference to the accompanying figures. Like elements in the various figures are denoted by like reference numerals for consistency. In the following detailed description, numerous specific details are set forth in order to provide a more thorough understanding. However, it will be apparent to one of ordinary skill in the art that the certain described aspects may be practiced without these specific details. In other instances, well-known features have not been described in detail to avoid unnecessarily complicating the description.

Certain terms are used throughout the following description and claims to refer to particular system components. As one skilled in the art will appreciate, different parties may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

A typical sensor, for example, a relative humidity (RH) sensor, operates stably within a recommended normal range (for a RH sensor, as a function of relative humidity and temperature). Long term exposure to conditions outside a normal range (for example, 85% RH/85degC) may temporarily offset the relative humidity signal. When exposure outside a normal range is limited in time, the sensor will slowly return to factory calibration. But, prolonged exposure to extreme conditions may accelerate aging, and increase long term offset (expressed in % RH/yr).

Generally, sensor aging is caused by issues related to a chemistry of the sensor. In a relative humidity sensor, the sensing element may be implemented as a capacitor where the dielectric is a polymer (a polyimide, or one of its derivatives), able to absorb moisture as a function of the relative humidity in air. A resulting change in permittivity of the polymer is detected (e.g., by a digital converter or other analog or digital circuitry) by the capacitance (or the change in capacitance) of the capacitor formed using the polymer. Prolonged exposure to extreme conditions can alter the sensor chemistry, causing a physiochemical change leading to drift in sensor performance.

Relative humidity (RH) is defined as the ratio of the partial pressure of water vapor to the saturated vapor pressure of water at a given temperature. While the partial pressure of water vapor is considered as a function of the moisture concentration, the saturated vapor pressure is a function of temperature only.

In one aspect, the disclosed embodiments use the integrated heater feature of a relative humidity sensor to derive a humidity offset needed by each singularly mounted, in-system device, independent of external references, for in-system calibration. Active calculation of slopes of one or both sensor outputs (humidity and temperature) is performed, and the respective output is compared to a pre-programmed threshold value while in a timed, or in a user-initiated, programmed control loop. The active calculation of slopes of one or both sensor outputs (humidity and temperature) is initially performed during fabrication, under controlled temperature and humidity conditions (referred to as an initial characterization). Later, in the field, over the lifetime of the device, in-system calibration can occur periodically (e.g., once or twice a year) at pre-selected intervals (or dates) programmed in the controller. Or, in-system calibration can occur based upon user selection, at any time, either by push button calibration initiation, or via personal device application, or through cloud connections (e.g., connections to a network).

In one example, FIG. 1 illustrates sensor hardware construction, in cross-section, of an integrated humidity and temperature sensor 100. Sensor 100 includes an exposed polymer element 110, a capacitor electrodes 120 (e.g., formed using a conductor, such as aluminum, copper, titanium, tantalum, a combination thereof and/or a nitride thereof), a dielectric layer 130 (e.g., one or more layers of silicon dioxide, silicon nitride, silicon oxynitride, low-k dielectric and/or mixtures thereof), and one or more integrated resistive heater elements 140 within a dielectric layer (e.g., one or more layers of silicon dioxide, silicon nitride, low-k dielectric and/or mixtures thereof) 150. Temperature sensor 100 may be formed over a semiconductor substrate (not shown) that may be used to form other electronic devices (such as, transistors). Multiple layers of conductors (used, for example, to interconnect electronic devices formed under or laterally spaced away from sensor 100) may be formed in interlevel dielectric layers (such as, one or more layers of silicon dioxide, silicon nitride, low-k dielectric and/or mixtures thereof) under dielectric layer 150. Sensor 100 may be used for measuring polymer dielectric change due to a presence of water vapor. Because the heater elements 140 are beneath the polymer element 110, water vapor is forced out of the polymer element 110, when the heater element(s) are activated, quickly reducing the relative humidity (% RH) to a consistently measurable level which can then be used directly for system calibration and offset correction.

Heating elements may be incorporated into an integrated humidity sensor to assist sensor recovery from condensation, or to reset the sensor when exposed to a volatile organic compound (VOC) (e.g., gas trapped in the sensor modifies sensor behavior, where exposing the sensor to high temperature degases the VOC). In one example, an existing heating element of an integrated humidity sensor can also be used to raise sensor temperature, and to reduce relative humidity, during consecutive humidity and temperature measurements.

Figure 2:
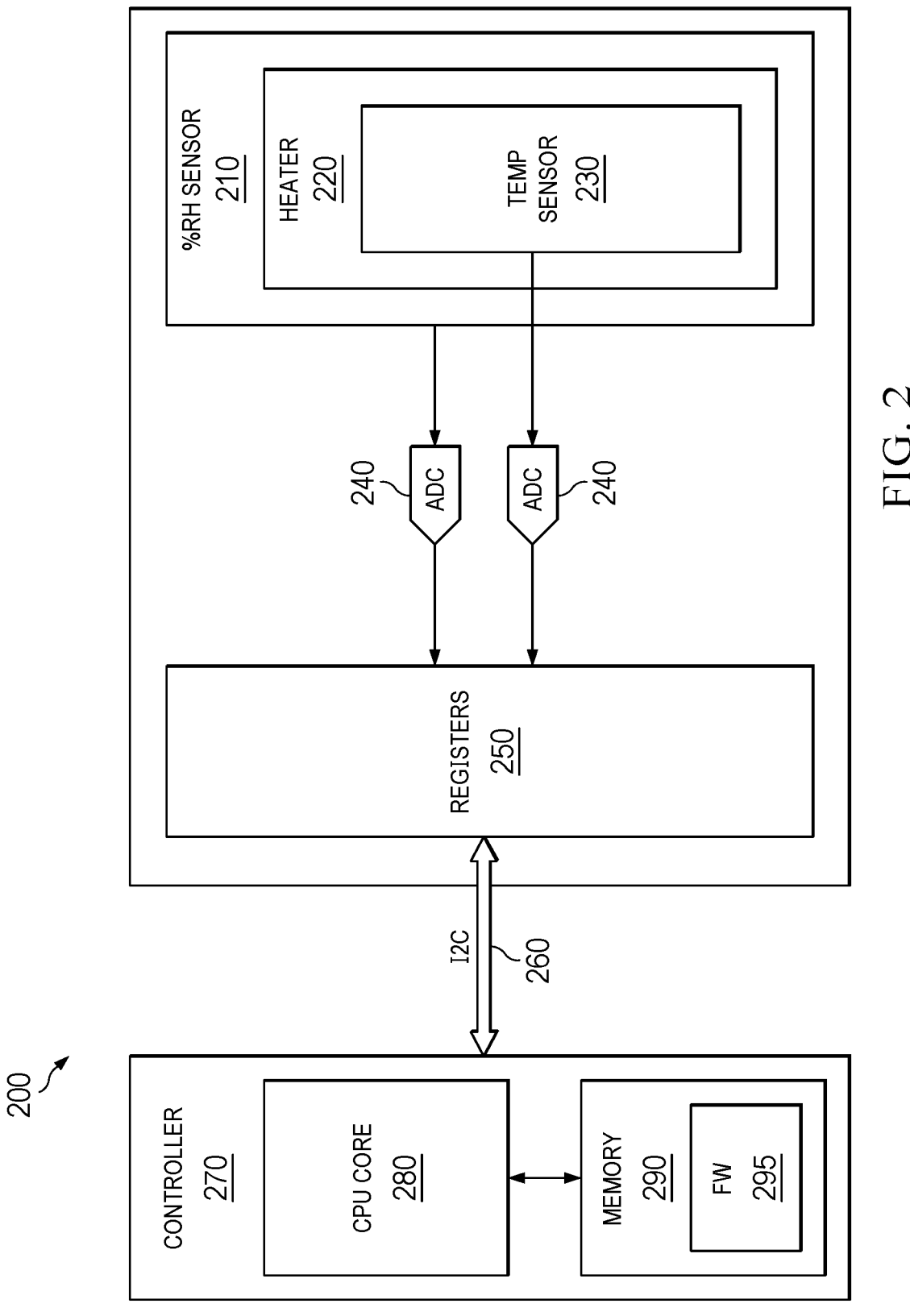
FIG. 2 illustrates a circuit block diagram of an example integrated humidity and temperature sensor, with accompanying controller, in accordance with various examples.

FIG. 2 illustrates a circuit block diagram of an example integrated humidity and temperature sensor 200, including a relative humidity sensing element 210, a heating element 220, a temperature sensing element 230, one or more analog-to-digital converters (ADC) 240, one or more registers 250, and a bus 260 (e.g., an Inter-Integrated Circuit (I2C) bus). The bus 260 provides, for example, synchronous, packet switched, single-ended, serial communication between the integrated humidity and temperature sensor 200 and a controller 270. The relative humidity sensing element 210, the heating element 220, and the temperature sensing element 230 may be implemented using integrated humidity and temperature sensor 100 of FIG. 1.

The integrated humidity and temperature sensor 200 may be used in systems to include thermostats, environmental/air quality monitors, gas sensor systems, HVAC subsystems, speakers, printers, sealed hard disk drives, medical devices, white goods and wireless sensors, to name a few applications. A common system level implementation of all of these applications generally includes a microcontroller or microprocessor to acquire the temperature and humidity data from the sensor and subsequently make control decisions based on the returned values.

In the example of FIG. 2, the controller 270 may include a processor 280 (such as, a digital signal processor, central processing unit (CPU), a microcontroller, microprocessor and/or other digital circuitry) and memory 290. The memory 290 may be separate from, but coupled to, the CPU 280, or the memory 290 may be provided within the CPU 280. Firmware 295 may be stored in memory 290. Upon execution of the firmware 295, by the CPU 280, the processor 280 performs some or all of the steps of the various methods of sensor calibration described herein. The controller 270 may be separate from the integrated humidity and temperature sensor 200, or the controller 270 may be integrated into the integrated humidity and temperature sensor 200. Nonetheless, the controller 270 would be configured for operation with the sensor 200 during application set-up, and therefore in any system embodiment of the described examples.

In one embodiment, the integrated humidity and temperature sensor 200 includes an ADC 240 for each sensor (e.g., the relative humidity sensor 210 and the temperature sensor 230) to convert an analog output signal from the respective sensor to a digital representation for storage in registers 250. In another embodiment, the integrated humidity and temperature sensor 200 may include one ADC with a front-end analog multiplexer through which a given temperature output signal is selected for conversion by the ADC. In these embodiments, the digital values (e.g., representing relative humidity and/or temperature) are stored in one or more locations in registers 250 and controller 270 may cause these registers to be read (and possibly rewritten into memory 290) for future processing. The heater 220 includes resistor type elements. With reference to FIG. 1, the heating element 220 may be coupled to conductor 120, which is connected to underlying conductor 140 via an interconnection. Based on the voltage/current applied to conductor 120, the heating coil 140 is energized to provide heat to the humidity sensor formed by conductors 120 and dielectric material 110.

In the example of FIG. 2, the controller 270 is in electrical communication with the register(s) 250. The controller 270 reads sensor values (e.g., converted to digital values by the ADCs) from the register(s) 250 and turns on the heating element 220 by writing to a particular heater control register. The firmware 295 causes controller 270 to read from and write to the register(s) 250. The sensor 200 converts signals/values from sensor 210, 230 to digital and stores the values in the register(s) 250. The heating element 200 also turns on upon the controller writing corresponding values to the heater register (e.g., writes a digital value to the register, which is converted to an analog voltage to be applied to the heating element).

FIG. 3 illustrates an example method for calibrating a relative humidity sensor 210 of an integrated humidity and temperature sensor 200. The method of FIG. 3 is referred to as an example calibration loop. Initially, the method described in FIG. 3 occurs during fabrication (e.g., at wafer-level testing, after device singulation and packaging, after final device testing, after module packaging and/or after the integrated solution is implemented into the final system) of the integrated humidity and temperature sensor 200, under controlled temperature and humidity conditions. This initial calibration (or initial characterization) may serve as a baseline for the particular sensor 200, or for a particular model of the sensor 200, or for a particular model of the sensor 200 as placed on each of different circuit board arrangements. Using this baseline, later in-system calibrations could be performed. However, the method of FIG. 3 is equally applicable to those later, in-system, calibrations occurring over the lifetime of the particular sensor 200. The later, in-system calibration(s) can occur periodically (e.g., once or twice a year) at pre-selected intervals (or dates) programmed in the controller. Or, in-system calibration can occur based upon user selection, at any time, either by push button calibration initiation, or via phone application, or through cloud connections. Some or all of the steps of FIG. 3 are performed by the CPU 280 upon execution of firmware 295.

In FIG. 3, in step 310, the controller 270 instructs a start of calibration (e.g., start of the calibration loop), and the heating element 220 is turned on, thereby increasing temperature of the integrated humidity and temperature sensor 200. To turn "on" the heating element 220, the CPU 280 writes a control value to a heater register, as part of the register(s) 250, which causes the sensor 200 to turn the heating element 220 on, as specified by the control value (e.g., different values stored in the register 250 may result in different heating conditions, such as temperature). At step 320, the controller 270 instructs that a temperature value and a humidity value, are measured/read (e.g., at a next prepro-grammed instance of time), from the temperature sensing element 230 and the relative humidity sensing element 210, respectively. More specifically, the CPU 280 writes a control value to the register(s) 250 to trigger an analog-to-digital conversion to occur, thereby causing the measured tempera-ture and/or humidity to be converted from an analog value to a digital value. At step 330, the converted digital values for temperature and/or relative humidity, and associated point in time, is written to the register(s) 250 by the respective ADCs 240.

Figure 4:
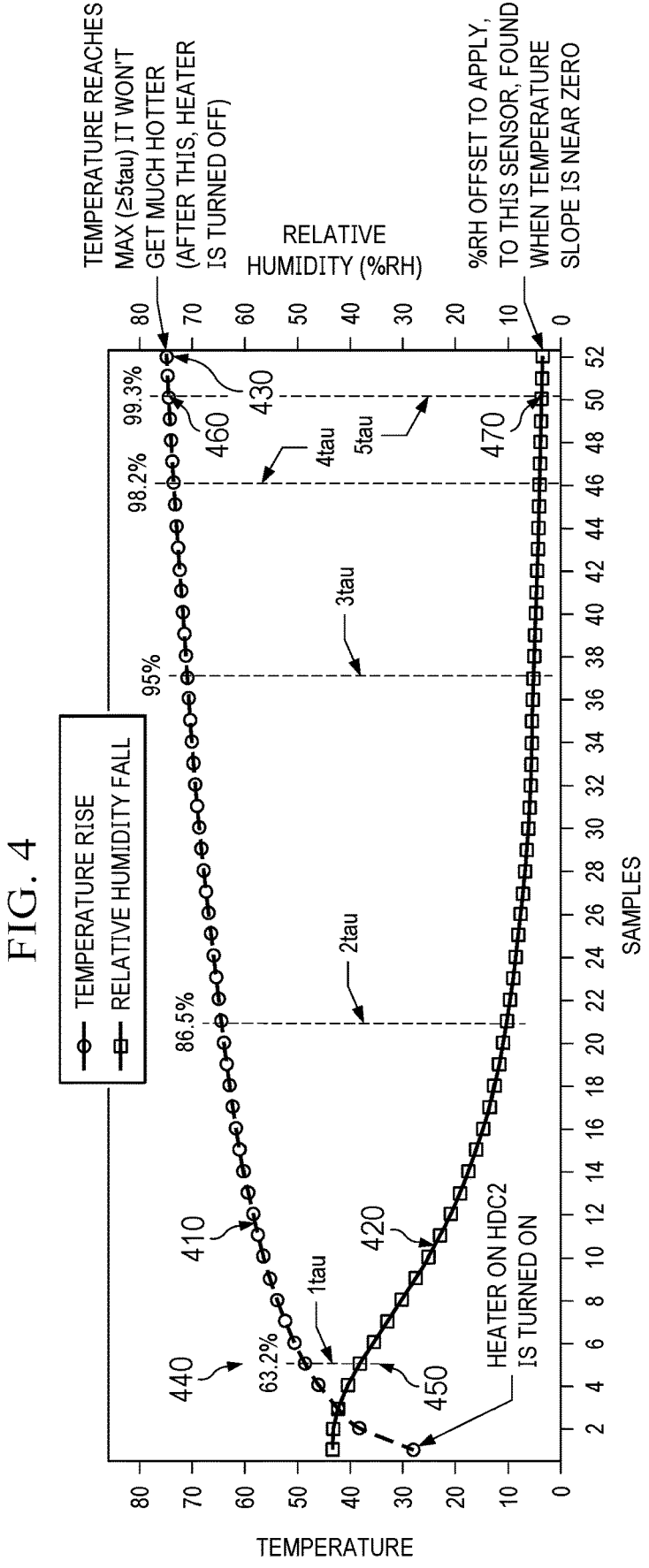
FIG. 4 is a graph illustrating temperature value rise, relative humidity fall, and temperature rise slope change, during heater operation, while performing calibration of a relative humidity sensor of an integrated humidity and temperature sensor, in accordance with various examples.

With the heating element 220 on, the temperature of the sensor 200 increases and the humidity decreases over time, thereby defining respective temperature and humidity slopes. FIG. 4 is a graph illustrating example temperature values 410 (from the temperature sensing element 230 while the heater is turned on) versus time. As shown, temperature increases asymptotically approaching a maximum tempera-ture value. FIG. 4 also includes relative humidity values 420 (from the relative humidity sensing element 210) versus time after the heater is turned on. Humidity decreases asymptotically towards a lower value. The X axis is "samples," with the samples occurring at relatively constant time intervals. The Y axis on the left side is temperature (for graph 410), and the Y axis on the right side is relative humidity (for graph 420). In the FIG. 4 graph, the tempera-ture values 410 rise as time progresses, and the relative humidity values fall.

At step 340, using the temperature and humidity output values, relative to the current point in time, the controller 270 calculates (e.g., using the currently measured value, previously measured value and the time between the two measurements) a slope of temperature value and a slope of the relative humidity value for the associated point in time, and writes the values to the register(s) 250. The controller 270 calculates a new slope value for temperature as the ratio of the difference in the current temperature value to the immediately preceding temperature value (from the previ-ous iteration of the method flow) divided by the difference in time from the previous iteration to the current iteration (or the difference in sample number). The update to the relative humidity slope is computed in the same way using the current and previous relative humidity values. During the calibration loop, as points in time are incrementally added, each of the slopes (e.g., slope of the temperature value rise and of the relative humidity value) begin to stabilize and approach zero.

At step 350, after each incremental point in time, the controller 270 determines whether one or both of the tem-perature slope and the relative humidity slope have reached respective threshold values. In one embodiment, only the slope of temperature is used, and it is this embodiment detailed hereafter for FIG. 3. It is understood, however, that either or both slopes could be incorporated into the step 350 determination. In another embodiment, the threshold value is 0 or nearly 0 (meaning that decision step 350 determines whether the slope or slopes have reached 0 (or almost 0). In other embodiments, threshold values could be 0.1, 0.05, or 0.01, which are pre-programmed.

At step 350, if the controller 270 determines that the slope of the temperature has not reached the pre-programmed threshold value, the calibration loop returns to step 320 for an additional iteration (at the next time step) of method steps 320, 330, 340 and 350. The time delta between each iteration may be, for example, around 100 microseconds.

If, at step 350, the controller 270 determines that the slope of the temperature has reached the pre-programmed thresh-old value, the method proceeds to step 360, in which the controller 270 reads the relative humidity value at the current point in time (e.g., the time at which the threshold value condition was satisfied). For example, in FIG. 4, the slope of the temperature may have reached the threshold value at point 430. At step 370, the controller 270 writes this relative humidity value as the relative humidity offset value (e.g., the relative humidity value corresponding to point 430). The relative humidity offset value is written to a register within registers 250. In one embodiment, a prior relative humidity offset value is overwritten by the new relative humidity offset value. In another embodiment, a new entry is stored (along with the corresponding time). The heating element 220 is turned off at this point. To turn off the heating element 220, the controller 270 writes a value to a register within the register(s) 250 to turn off the heating element 220.

After step 370, the calibration loop is complete. Accord-ingly, during "normal" (non-calibration) operation thereaf-ter, the controller 270 subtracts the relative humidity offset value from a newly acquired (most recently stored) relative humidity value (sensed) to thereby provide a more accurate relative humidity value.

The calibration loop method steps detailed above provide an integrated humidity and temperature sensor automated calibration solution generally described as follows. First, the heater element, inside the integrated humidity and tempera-ture sensor, is turned on. As the sensor heats up, the sensed temperature and relative humidity (% RH) values are read/measured. As values of temperature and relative humidity are returned and recorded, the controller updates a calcula-tion of one or both of the slope of the temperature value rise and of the relative humidity fall. Then, a determination is made when the slopes of the changing temperature and/or relative humidity values are at or very close to zero. In practical application, the slopes of temperature and/or relative humidity are at or close to zero when the temperature of the integrated humidity and temperature sensor is near or at its maximum possible temperature.

When the slopes of temperature and/or relative humidity are at or close to zero, the % RH value returned is the offset for that particular integrated humidity and temperature sensor. At this point, the heater is turned off and the % RH value returned can later be subtracted directly from the % RH measured value, during normal operation, and returned as the corrected % RH value for the system.

In an alternative embodiment, slope of the temperature value rise and/or the humidity value fall is not necessary. At step 350, a termination (or determination) condition is satisfied when the current temperature (or humidity) value is equal or very close to the previous temperature (or humidity value). In another alternative embodiment, the determination condition, at step 350, is a pre-determined (e.g., maximum) temperature value for the sensor. In this alternative embodiment, the threshold values could be 0.01%, 0.1%, 0.5%, or 1% of this pre-determined temperature value. The associated relative humidity value occurring at the point in time of reaching the pre-determined temperature value is the relative humidity offset value.

As detailed above, the slope of the relative humidity value curve 420, during heater operation, is not necessary, but can also be calculated, at each of the various, preprogrammed points in time, and used to determine the relative humidity offset value. In this aspect, when the fall in relative humidity slope reaches a threshold value (e.g., relative to the relative humidity slope being at, or close to, zero), the heater is switched off and the relative humidity value at that point in time is the relative humidity offset value to apply. In certain aspects, calculation and use of the relative humidity slope is used for redundancy, and as a check, but calculation and use of both slopes is not necessary, as either, alone, provides the similar results, as does the alternative embodiments detailed above.

The rising temperature and the falling humidity generally have the same shape as the increasing or decreasing voltage of a resistor-capacitor (RC) circuit. An RC time constant, tau, is the time constant (in seconds) of an RC circuit, and is equal to the product of the circuit resistance and the circuit capacitance. Generally, for RC circuits, 1-tau is the time required to charge the capacitor, through the resistor, from an initial charge voltage of zero to approximately 63.2% of the value of an applied DC voltage. Therefore, 1-tau occurs at 63.2% of applied DC voltage, and 2-tau, 3-tau, 4-tau, and 5-tau occur at 86.5%, 95%, 98.2%, and 99.3%, respectively, of the applied voltage.

FIG. 4 illustrates "tau" time constants associated with the temperature value curve 410 and the relative humidity value curve 420. For the subject matter of the described examples, the temperature value at 1-tau, 2-tau, 3-tau, 4-tau, and 5-tau represents 63.2%, 86.5%, 95%, 98.2%, and 99.3%, respectively, of the maximum temperature reached by the integrated humidity and temperature sensor 200.

In one aspect, use of the temperature values associated with each tau constant, as a percentage of maximum temperature reached for the integrated humidity and temperature sensor 200, could serve as an alternative method to determining the relative humidity (% RH) offset for the sensor during later (e.g., after initial characterization at fabrication), in-system calibration in the field. That is, after an initial characterization of an integrated humidity and temperature sensor (e.g., determining the temperature and relative humidity curves, during sensor fabrication, as shown in FIG. 4, and where maximum temperature reached is determined), tau time constant percentages of the maximum temperature value reached are determined and associated to the temperature and relative humidity curves. For the example illustrated by FIG. 4, the "1-tau" value is set to be the value where the measured temperature is equal to 63.2% of the maximum temperature (e.g., the 1-tau value, point 440, is calculated by 75°×63.2%=47.4°. The relative humidity value associated with the 1-tau temperature value is also determined, shown as value 450 in FIG. 4. As a further example, the 5-tau value (point 460 on the temperature curve 410) is set to be the value where the measured temperature is equal to 99.3% of the maximum temperature (75°× 99.3%=74.5°. The relative humidity value 470 associated with the 5-tau temperature value is also determined, as shown in FIG. 4. The controller instructs the determination (or reading) of the above, for all of tau constants (1-tau, 2-tau, 3-tau, 4-tau, 5-tau), and the respective temperature and relative humidity values are recorded to the register(s) 250, as is all of the initial characterization information.

In this alternative example, used during in-system calibration of the integrated humidity and temperature sensor in the field (e.g., with initial characterization information recorded to the register(s) 250), the method of in-system calibration may include steps as shown in the example of FIG. 5, which could be referred to as an in-system calibration loop. As detailed above, in one embodiment the in-system calibration relies upon the baseline (or initial characterization) for the particular sensor 200 (as placed on a respective board layout). The later, in-system calibration(s) can occur periodically (e.g., once or twice a year) at pre-selected intervals (or dates) programmed in the controller. Or, in-system calibration can occur based upon user selection, at any time, either by push button calibration initiation, or via personal device application, or through cloud connections.

As illustrated in FIG. 4, the slope of temperature rise is relatively close to zero at both 4 tau and 5 tau. This provides, practically, that a later in-system calibration can determine a relatively accurate relative humidity offset without heating the integrated humidity and temperature sensor to a maximum temperature, or until the slope of temperature rise is at, or very close to zero, thus saving calibration time and heat energy. That is, knowing the maximum temperature reached during initial characterization, and/or at what point the slope of temperature rise approaches zero, allows for an approximate, but relatively accurate, relative humidity offset determination without heating the integrated humidity and temperature sensor to an ultimate end (or absolute maximum temperature). This alternative aspect may be desirable, for later, in-system calibration, when use of sensor does not provide sufficient power capacity to heat the specific sensor device to maximum temperature (e.g., in a battery powered device).

In step 510 of FIG. 5, the controller 270 instructs a start of calibration (e.g., start of the in-system calibration loop), and the heating element 220 is turned on, thereby increasing temperature of the integrated humidity and temperature sensor 200. To turn on the heating element 220, the CPU 280 writes a control value to a heater register, as part of the register(s) 250, which causes the sensor 200 to turn the heating element 220 on, as specified by the control value (e.g., different values stored in the register 250 may result in different heating conditions, such as temperature). Initiation of in-system calibration can occur anytime during normal sensor 200 operation.

At step 520, the controller 270 instructs that a temperature value and a humidity value are measured/read (e.g., at a next preprogrammed instance of time) from the temperature sensing element 230 and the relative humidity sensing element 210, respectively. More specifically, the CPU 280 writes a control value to the register(s) 250 to trigger and analog-to-digital conversion to occur, thereby causing the measured temperature and/or humidity to be converted from an analog value to a digital value. At step 530, the converted digital values for temperature and/or relative humidity, and associated point in time, is written to the register(s) 250 by the respective ADCs 240.

At step 540, using the temperature and humidity output values, relative to the point in time, the controller 270 calculates a slope of temperature value rise and/or a slope of the relative humidity value for the associated point in time, and writes the value to the register(s) 250. Step 540 is an optional step, and is not necessary in certain embodiments.

At step 550, after each incremental point in time, the controller 270 determines whether the temperature value sensed is equal to or greater than the temperature value associated with the pre-programmed tau constant (e.g., if using the FIG. 4 embodiment, and if 5-tau is preprogrammed, the controller determines whether the temperature value sensed has reached approximately 74.5° or another value designated by an end-user, the system that incorporates the sensors or by specification). If no, the calibration loop returns to step 520 for an additional iteration (at the next time step) of method steps 520, 530, 540 and 550.

If, at step 550, the controller 270 determines that the temperature value sensed is equal to or greater than the temperature value associated with the pre-programmed tau constant, the method proceeds to step 560, where the controller 270 reads the relative humidity value at the current point in time, and at step 560, the controller 270 writes this relative humidity value as the relative humidity offset value. Finally, at step 370, the relative humidity value, representing the relative humidity offset value, is written to registers, any prior relative humidity offset value is overwritten (or stored in an alternative location), and the heating element 220 is turned off. To turn off the heating element 220, the controller 270 writes a value to a register within the register(s) 250 to turn off the heating element 220.

After step 570, the calibration loop is complete. Accordingly, during normal operation thereafter, controller 270 subtracts the new relative humidity offset value from a newly acquired relative humidity value (sensed) to thereby provide a more accurate relative humidity value.

In summary, the in-system calibration loop method steps of FIG. 5 provide an integrated humidity and temperature sensor automated calibration solution generally described as follows. First, the heater element, inside the integrated humidity and temperature sensor, is turned on. As the sensor heats up, the sensed temperature and relative humidity (% RH) values are read/measured. As values of temperature and relative humidity are returned and recorded, the controller assesses whether the temperature value sensed is equal or greater than the temperature value associated with the pre-programmed tau constant. At that point in time, the relative humidity value associated with the temperature value is determined, and that relative humidity value becomes the new relative humidity offset value for that particular integrated humidity and temperature sensor. The heating element is turned off and the relative humidity value returned can later be subtracted directly from the relative humidity value measured (sensed), during normal operation, and returned as the corrected relative humidity value for the system.

In another aspect, FIG. 6 illustrates an example of an association table attributable to a specific humidity and temperature sensor. Methods of the described examples operate over an entire voltage input range of any specific sensor system. In some embodiments, when performing an initial characterization, a highest possible operating voltage is used (e.g., 3.3 v), so that a true maximum temperature is reached. When a specific sensor operates at a lower voltage, a lower current is realized, and therefore the specific sensor might be limited to a lower final, maximum temperature attained. Operating at a lower supply voltage will affect in-system calibration of the sensor, because the supply voltage may not be high enough to effectively energize the heating coil to reach a true maximum temperature. Because of this, the system may not be able to determine an accurate relative humidity offset. For example, the heating element of the sensor is a resistive element, and when switched on, the input voltage to the sensor is applied to the resistive element, causing current to flow, which produces the heat. In accordance, with Ohm's Law, voltage and current are directly proportional. Accordingly, raising or lowering the input voltage results in more or less current (and resulting heat), respectively, when operating the heating element.

To overcome this potential issue, a simple characterization matrix 600, as illustrated in FIG. 6, can be created from calibration runs of an integrated humidity and temperature sensor, at various possible operating voltages. Based on the characterization matrix 600, a divisor (such as divisor 660) is determined that allows for an accurate determination of relative humidity offset, by accounting for an entire voltage range of the specific sensor.

In FIG. 6, calibration runs were performed on a sample integrated humidity and temperature sensor at various operating voltages 610. Each row 615 of characterization matrix 600 illustrates operating information for each of the operating voltages. For each operating voltage 610, characterization matrix 600 includes values for: peak current (mA) 620, stable current (mA) 630, final temperature 640, final relative humidity (e.g., relative humidity offset value) 650, a final relative humidity value divisor 660, a resulting relative humidity offset value to apply 670, and a variance from a known good value 680.

For example, according to characterization matrix 600, for this specific sensor, operation at 3.3 v (column 610) results in a final temperature (column 640) of 73.48°. As expected, the highest final temperature occurs when the operating voltage is the highest, and use of the highest final temperature to determine a relative humidity offset is considered the most accurate offset value. Accordingly, operation at 3.3 v (row 615) results in a final relative humidity offset (column 670), determined from methods described herein, of 9.82%.

For this specific sensor, operation at 1.8 v (row 685) results in a final temperature reached (by temperature sensors 230) of 39.47°, and a resulting final relative humidity (column 650) of 30.59%. This relative humidity (39.59%) is high, and is a result of only 39.47° being reached as a final temperature.

Calculation of a divisor 660, for each operating voltage 610, that could associate a determined final relative humidity 650, for a sensor operating at a lower operating voltage, to obtain a correct relative humidity offset value, is advantageous.

In FIG. 6, a divisor is calculated, using the power consumed by the heater, and this divisor can be used to improve the relative humidity offset determination for sensors systems operating at lower supply voltages. For example, in row 615, the total power available to the heater is determined by multiplying the operating temperature by the current drawn by the heater (3.3 v×99 mA=326.7 mW). In row 685, total power available when the supply voltage is 1.8 V is 97.2 mW (1.8 v×54 mA=97.2 mW). Therefore, operation at 1.8 v results is approximately ⅓ the power of operation at 3.3 v. Accordingly, inverting this relationship results in a final relative humidity value divisor (column 660) of 3. Taking the final relative humidity value (column 650), read while operating at 1.8 v (e.g., 30.59), and dividing that value by the divisor of 3, results in an offset value (column 670) of approximately 10.2. Comparing the resulting offset value of approximately 10.2, to the resulting relative humidity offset of 9.82, determined under the best conditions provided herein (e.g., highest operating voltage), results in a variance from known good value (column 680) of only 0.266 (a very good approximation).

In FIG. 6, each of the other final relative humidity value divisors are determined similarly, and each is stored in the register(s) 250. As an additional step during an in-system calibration of an integrated humidity and temperature sensor in the field, if the in-system calibration occurs at an operating voltage lower than 3.3 v, a finally determined relative humidity offset 650 will be adjusted by the respectively appropriate divisor 660 to arrive at a resulting relative humidity offset value to apply. In some examples, each of the values depicted in FIG. 6 (or equivalent values depending on the sensor system and operating voltages) are stored in register 250. In other examples, more or fewer values are included in the characterization matrix and more or fewer values are stored in register 250.

While the disclosure has been described with reference to illustrative examples, this description is not intended to be construed in a limiting sense. Various other examples of the disclosure will be apparent to persons skilled in the art upon reference to this description.

Although method steps may be presented and described herein in a sequential fashion, one or more of the steps shown and described may be omitted, repeated, performed concurrently, and/or performed in a different order than the order shown in the figures and/or described herein. Accordingly, aspects described should not be considered limited to the specific ordering of steps shown in the figures and/or described herein.

In this description, the term "and/or" (when used in a form such as A, B and/or C) refers to any combination or subset of A, B, C, such as: (a) A alone; (b) B alone; (c) C alone; (d) A with B; (e) A with C; (f) B with C; and (g) A with B and with C. Also, as used herein, the phrase "at least one of A or B" (or "at least one of A and B") refers to implementations including any of: (a) at least one A; (b) at least one B; and (c) at least one A and at least one B. A device that is "configured to" perform a task or function may be configured (e.g., programmed and/or hardwired) at a time of manufacturing by a manufacturer to perform the function and/or may be configurable (or re-configurable) by a user after manufacturing to perform the function and/or other additional or alternative functions. The configuring may be through firmware and/or software programming of the device, through a construction and/or layout of hardware components and interconnections of the device, or a combination thereof. As used herein, the terms "terminal", "node", "interconnection", "pin", "ball" and "lead" are used interchangeably. Unless specifically stated to the contrary, these terms are generally used to mean an interconnection between or a terminus of a device element, a circuit element, an integrated circuit, a device or other electronics or semiconductor component. While certain elements of the described examples are included in an integrated circuit and other elements are external to the integrated circuit, in other example embodiments, additional or fewer features may be incorporated into the integrated circuit. In addition, some or all of the features illustrated as being external to the integrated circuit may be included in the integrated circuit and/or some features illustrated as being internal to the integrated circuit may be incorporated outside of the integrated. As used herein, the term "integrated circuit" means one or more circuits that are: (i) incorporated in/over a semiconductor substrate; (ii) incorporated in a single semiconductor package; (iii) incorporated into the same module; and/or (iv) incorporated in/on the same printed circuit board. Unless otherwise stated, "about," "approximately," or "substantially" preceding a value means +/−10 percent of the stated value, or, if the value is zero, a reasonable range of values around zero.

It is therefore contemplated that the appended claims be interpreted to embrace all such variations and modifications of the aspects described.

What is claimed is:

1. A method comprising:

operating a heating element;

calculating a temperature rise slope value as a function of a difference between a first temperature measurement and a second temperature measurement over a time interval, the first and second temperature measurements taken while operating the heating element;

comparing the temperature rise slope value to a threshold value;

determining a first relative humidity measurement that was taken by a relative humidity sensor at a time when the temperature rise slope value is less than the threshold value;

calculating a humidity falling slope value as a function of a difference between the first relative humidity measurement and a second relative humidity measurement over the time interval, the first and second relative humidity measurements taken while operating the heating element;

determining a first offset value based on the temperature rise slope value and the humidity falling slope value;

determining an operating voltage of the heating element;

dividing the first offset value by a divisor value according to the operating voltage to generate a second offset value; and calibrating the relative humidity sensor using the second offset value.

2. The method of claim 1, wherein calibrating the relative humidity sensor includes subtracting the second offset value from a second relative humidity measurement taken by the relative humidity sensor.

3. The method of claim 1, wherein generating the second offset value includes storing the second offset value to a register.

4. The method of claim 1, wherein the threshold value is 0.1 or less.

5. The method of claim 1, wherein the threshold value is 0.01.

6. The method of claim 1, wherein the threshold value is zero.

7. A controller comprising;

memory; and a processor coupled to the memory and configured to:

calculate a rising temperature condition value as a function of a difference between a first temperature measurement and a second temperature measurement, the first and second temperature measurements taken by a temperature sensor while a heating element is operated;

compare the temperature condition value to a threshold value;

calculate a falling humidity condition value as a function of a difference between a first relative humidity measurement and a second relative humidity measurement, the first and second relative humidity measurements taken by a relative humidity sensor while the heating element is operated;

determine a first offset value based on the rising temperature condition value and the falling humidity condition value;

determine an operating voltage of the heating element;

divide the first offset value by a divisor value according to the operating voltage to generate a second offset value; and calibrate the relative humidity sensor using the second offset value.

8. The controller of claim 7, wherein the processor is configured to:

store in the memory the second offset value, the first relative humidity measurement, and the second relative humidity measurement taken by the relative humidity sensor; and subtract the second offset value from the second relative humidity measurement to calibrate the relative humidity sensor.

9. The controller of claim 7, wherein the processor is configured to calculate the rising temperature condition value as a function of a difference between the first temperature measurement and the second temperature measurement over a time interval, indicating a slope of temperatures over the time interval.

10. The controller of claim 7, wherein the threshold value is zero.

11. The controller of claim 7, wherein the threshold value is less than 0.1.

12. A system comprising:

a relative humidity sensor formed over a semiconductor substrate;

a temperature sensor formed over the semiconductor substrate;

a heating element formed over the semiconductor substrate; and a controller coupled to the relative humidity sensor, the temperature sensor, and the heating element, the controller configured to:

control operation of the heating element;

receive first and second temperature measurements taken during a time interval of operating the heating element;

calculate a rate of increase of temperature as a function of a difference between the first and second temperature measurements over the time interval;

determine a first relative humidity measurement that was taken by the relative humidity sensor at a time when the rate of change increase of temperature is less than a threshold value;

calculate a humidity falling slope value as a function of a difference between the first relative humidity measurement and a second relative humidity measurement over the time interval, the first and second relative humidity measurements taken while operating the heating element;

determine a first offset value based on the rate of increase of temperature and the humidity falling slope value;

determine an operating voltage of the heating element;

divide the first offset value by a divisor value according to the operating voltage to generate a second offset value; and calibrate the relative humidity sensor using the second offset value.

13. The system of claim 12, wherein the threshold value is less than 0.1.

14. The system of claim 12, wherein the controller is configured to:

calculate a relative humidity condition value as a function of a difference between a second relative humidity measurement and a third relative humidity measurement;

compare the relative humidity condition value to a second threshold value; and determine that the first relative humidity measurement was taken at a time when the relative humidity condition value is less than the second threshold value.

15. The system of claim 14, wherein the controller is further configured to calculate the relative humidity condition value as a function of the difference between the second relative humidity measurement and the relative third humidity measurement over the time interval, indicating a rate of change of relative humidity.

16. The system of claim 14, wherein the threshold value is less than 0.01.

* * * * *